United States Patent [19]

Arnold et al.

[11] Patent Number: 4,626,506

[45] Date of Patent: Dec. 2, 1986

[54] PROCESS AND DEVICE FOR THE DETERMINATION OF CELLS SECRETING CELLULAR CONTENTS

[75] Inventors: William M. Arnold, Aachen; Ulrich Zimmermann, Hürtgenwald-Gey, both of Fed. Rep. of Germany

[73] Assignee: Kernforschungsanlage Jülich, Julich, Fed. Rep. of Germany

[21] Appl. No.: 625,523

[22] Filed: Jun. 28, 1984

[30] Foreign Application Priority Data

Jun. 29, 1983 [DE] Fed. Rep. of Germany ....... 3323415

[51] Int. Cl.$^4$ ............................................ C12N 13/00
[52] U.S. Cl. ........................................ 435/173; 424/3; 435/4; 436/149; 436/151; 436/806
[58] Field of Search ................. 128/1.3; 424/3; 435/4, 435/173; 436/149, 151, 806

[56] References Cited

U.S. PATENT DOCUMENTS 3,418,500 12/1968 Davis ................................ 310/308

FOREIGN PATENT DOCUMENTS 1096280 6/1984 U.S.S.R. ............................. 435/173

OTHER PUBLICATIONS

Laboratory Equipment Digest, vol. 18, No. 10, (Oct. 1980), pp. 91-93.

*Primary Examiner*—Christine M. Nucker
*Assistant Examiner*—Stephen C. Wieder
*Attorney, Agent, or Firm*—Pahl, Lorusso & Loud

[57] ABSTRACT

Disclosed is a process and device for determining which cells of a suspension containing cells of the same species and genus are secreting cellular substances. Such determinations are made by exposing the cells to rotating electrical field forces of variable rotational speed and differentiating the cells secreting the cellular substances from the other cells by means of their rotational behavior which differs from that of the other cells.

5 Claims, 1 Drawing Figure

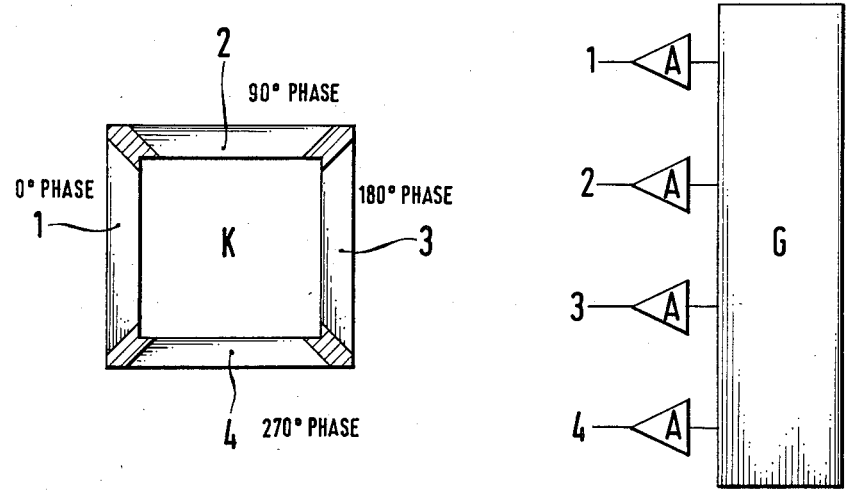

PROCESS AND DEVICE FOR THE DETERMINATION OF CELLS SECRETING CELLULAR CONTENTS

BACKGROUND OF THE INVENTION

This invention concerns a process for the determination of cells secreting cellular contents such as proteins and/or glycoproteins, hormones, or growth factors, from a medium containing these cells and cells of the same species or genus. The invention also concerns a device for implementing this process.

In a number of applications in the biological, pharmacological, and medical field, there is a need to be able to differentiate cells secreting cellular substances from cells of the same species and genus. Thus, for example, it is of considerable importance for the formation of monoclonal antibodies to determine stimulated lymphocytes from a suspension of stimulated lymphocytes and unstimulated lymphocytes.

Certain lymphocytes form antibodies (glycoproteins) against foreign substances in the organism, such as a foreign protein, which is injected into the bloodstream. If such lymphocytes stimulated for the formation and release of antibodies are fused with a tumor cell, such as a myeloma cell, there is a chance that a so-called hybidoma cell will be formed which has the features of both parent components. This cell produces antibodies, specifically only against the foreign substance involved (so-called monoclonal antibodies). It is practically immortal and can multiply permanently in nutrient media, in contrast to a normal differentiated cell such as the lymphocyte.

However, since only a very small number of the many lymphocytes found in the lymphatic system are stimulated, and since only the stimulated lymphocytes should be supplied for fusion if possible, the stimulated lymphocytes must be separated from the unstimulated lymphocytes in a selection process. However, there are difficulties here even in recognizing the stimulated lymphocytes, since they cannot be differentiated from the unstimulated lymphocytes by microscopic observation.

As another example, it might also be mentioned that some microorganisms are able to lyse living yeast cultures by secreting certain cellular substances (primarily glycoproteins). These toxins are called "killer factors". "Killer yeasts" can cause difficulties in the production of beer. Even with a small degree of contamination, they produce changes in the fermentation and the quality of the beer. The existence and consequences of killer reactions have been established in brewer's yeasts, wine yeasts, baking yeasts, and also with other species of cells, such as Hansenula, Pichia, Deberyomyces, Kluyveromyces, Candida, and Torulopsis, for example.

In the cases mentioned, and in many others, it is first a question of recognizing the secreting cells in order to be able to initiate other measures. These other measures can consist of then segregating these cells, as in the case of the stimulated lymphocytes, for example. In the case of killer yeast cells, the recognition of such cells is useful initially for the monitoring of the fermentation process. This in turn can lead to the introduction of measures to avoid the contamination.

It is therefore a principal object of the present invention to provide a process which makes it possible to determine cells secreting cellular substances such as proteins and glycoproteins, hormones, or growth factors from a suspension containing cells of the same species and genus.

It is also an object of this invention to provide a device for implementing the process.

SUMMARY OF THE INVENTION

In the process and device of the present invention cells are exposed to rotating electrical field forces of variable rotational speed, and the cells secreting the cellular substances are differentiated from the other cells by means of their rotational behavior which differs from that of the other cells.

In another embodiment, the secreting cells are differentiated by adjusting the secreting cells to their maximum rotational speed by the use of the appropriate characteristic frequency of the rotating electric field.

These and other features and objects of the present invention will be more fully understood from the following detailed description which should be read in the light of the accompanying drawings.

BRIEF DESCRIPTION OF THE DRAWING

The FIGURE is a schematic view of a device for carrying out the process of the present invention.

DETAILED DESCRIPTION OF THE PREFERRED EMBODIMENTS

According to the present invention, a process is provided which makes it possible to determine cells that are secreting cellular substances such as proteins and glycoproteins, hormones or growth factors from cells of the same species and genus in suspension. Such determinations are achieved by exposing the cells to rotating electrical field forces of variable rotational speed and differentiating the cells secreting the cellular substances from the other cells by means of their rotational behavior which differs from that of the other cells.

The process pursuant to the invention is based on the discovery that cells which secrete cellular substances such as proteins and/or glycoproteins, hormones, or the growth-controlling substances (so-called "growth factors") show a rotational behavior in a rotating electrical field different from that shown by nonsecreting cells of the same species or genus, which can be attributed to a modification of the membrane as a result of the passage of the cellular substances.

It is known from Z. Naturforsch. 37 c, 908–915 (1982), "Rotating-Field-Induced Rotation and Measurement of the Membrane Capacitance of Single Mesophyll Cells of Avena Sativa", W. M. Arnold and U. Zimmermann, that individual cells, protoplasts in this case, can be brought into rotation in a rotating electrical field, which is produced for example by four electrodes, each displaced by 90° from the others. It is also known that individual cells of a specific cell species can be placed in maximum rotational speed at a specific frequency of the rotating field (the so-called characteristic frequency).

The characteristic frequency for a specific cell species actually depends on other parameters such as: the intensity of the rotating electrical field and the environmental conditions for the cells, the conductivity of the medium in which the cells are found, and the temperature of the medium. However, only the different rotational behavior of the cells to be differentiated is involved in a differentiation measurement, as for example the different characteristic frequency of the cells secreting internal substances and of the other cells of the same species and genus. The conductivity of the medium, which is appropriately in a range from 5 to $500 \times 10^{-6}$ S$\times$cm$^{-1}$, and preferably 5 to $50 \times 10^{-6}$ S$\times$cm$^{-1}$, is therefore of only subordinate importance for the differentiation of the cells themselves. The temperature of the medium must also be adjusted primarily so that the cells are not damaged, on the one hand, but also on the other hand so that a formation and secretion of the cellular substances to be secreted is possible.

An appropriate variation of the process pursuant to the invention consists of differentiating the secreting cells by adjusting them to their maximum rotational speed by use of the characteristic frequency of the rotating electrical field determined for the cells in a given medium. The cells in suspension in this case are observed under the microscope with regard to their rotational behavior, whereby it is initially most easily observed during the change of the frequency range of the rotating field, at what frequency the majority of the cells, namely the other cells, rotate with their highest speed. By further changing of the frequency of the rotating field and adjusting to the characteristic frequency of the secreting cells, however, these are generally easy to differentiate visually from the other cells after practice. It is assumed here that the specialist in a practical case will know the characteristic frequencies of the secreting cells and of the other cells, so that the differentiation of the cells is thereby facilitated. Although a natural spread of the properties of the cells is present, as in all biological populations, and this spread is therefore also found in the rotational behavior of the cells, this is no hindrance in general to a differentiation of the particles.

According to the present invention, an apparatus for implementing the above-described process is provided in which at least three electrodes, forming an intermediate space between them for a chamber containing the cells, or forming a container, or extending into a chamber provided to hold the cells, are arranged so that the chamber or container space is exposed to a rotating electrical field produced by the electrodes, and by a device which can be connected to the electrodes to produce a rotating field of variable rotational frequency. The intensity of the rotating field is also appropriately variable. It should be in such a range that approximately 1 to 1000 V/cm is produced in the chamber. The frequency range should lie in the range between 1 Hz and 1 GHz. In carrying out the process pursuant to the invention, an intensity is chosen which lies beneath the electrical breakdown voltage for the cells to be treated.

It has been found that it is also appropriate for the electrical voltages producing the rotating field to be sinusoidal. However, it is also possible to produce the rotating field by square-wave voltages or by pulsed voltages or voltages of another form.

Four electrodes are provided which are positioned on a base plate of electrically nonconductive material, not shown in the drawing, so that they form the lateral walls of the chamber K provided to hold the cells. The electrodes are cemented to one another and to the base plate by means of an electrically insulating adhesive. The electrode length and thus the length of the lateral walls of the chamber is 1 mm, and the height of the electrodes is 0.2 mm. The rectangular chamber K open at the top thus has the lateral dimension of 1 mm and the height of 0.2 mm. The electrodes consisting of platinum foil are connected to the amplifiers V of the generator G in the order shown in the drawing. The voltages transmitted by the amplifiers, as also seen in the drawing, are shifted in phase by 90° in each case, whereby a rotating electrical field is produced in the chamber.

In all of the following examples the following conditions exist: stimulated B-lymphocytes were produced by immunizing a mouse with sheep erythrocytes. The lymphocyte fraction extracted from the mouse contained the stimulated lymphocytes together with unstimulated lymphocytes. The lymphocyte fraction was placed in a layer of erythrocytes from the sheep and later the stimulated lymphocytes, i.e., those secreting the antibody, were again withdrawn by micropipette. The stimulated lymphocytes could be recognized by the fact that a group of lysed erythrocytes had formed around them (by the method described in the "Annales of Institute Pasteur, 1975" (Zagury and coworkers)).

In this way, stimulated lymphocytes were obtained which secreted an antibody against the erythrocytes of sheep. A portion of these stimulated lymphocytes was mixed with at least the same quantity of unstimulated lymphocytes, which had also been taken by micropipette from the erythrocyte layer.

The mixture of lymphocytes, before it was placed in the rotation chamber K, was washed three times in a medium of low conductivity (0.3 M mannitol with traces of sodium chloride as electrolyte).

EXAMPLE 1

Approximately 10 $\mu$l of a suspension containing the mixture of lymphocytes was placed in the rotation chamber K. The conductivity of the suspension was $18.4 \times 10^{-6}$ S/cm$^{-1}$, and the temperature was 35° C. The suspension was exposed to a rotating electrical field with an intensity of approximately 100 V/cm.

The stimulated lymphocytes could be recognized under the microscope by their higher rotational speed at a rotational frequency of approximately $38 \pm 5$ kHz, and could be differentiated from the other lymphocytes, which were brought to their maximum rotational speed at a rotational frequency of approximately $25 \pm 5$ kHz.

The lymphocytes recognized as stimulated lymphocytes on the basis of their rotational behavior were withdrawn from the rotation chamber by micropipette and were again placed in a bed of sheep erythrocytes as a check. The check test confirmed that they were stimulated lymphocytes.

EXAMPLE 2

As described in Example 1, a mixture of stimulated and unstimulated lymphocytes was exposed to a rotating electrical field. The conductivity of the suspension containing the lymphocytes, however, was $5.2 \times 10^{-6}$ S/cm$^{-1}$.

In this case also, the stimulated lymphocytes were recognized by their maximum rotational speed. The corresponding rotational frequency was approximately $12 \pm 3$ kHz. The rotational frequency at which the unstimulated lymphocytes rotated most rapidly was approximately $7 \pm 2$ kHz.

The foregoing invention has been described with reference to its preferred embodiments. Although variations and modifications will occur to those skilled in the art, it is intended that such variations and modifications fall within the scope of the apended claims.

What is claimed is:

1. Process for the determination of cells secreting cellular contents such as proteins and/or glycoproteins, hormones, or growth factors, from a medium containing said secreting cells and other cells of the same species or genus, comprising the steps of:

exposing the cells to rotating electrical field forces of variable rotational speeds;

differentiating the first group of cells secreting cellular contents from said other cells by means of the rotational behavior of said secreting cells which differs from that of said other cells.

2. Process pursuant to claim 1 wherein the secreting cells are differentiated from the other cells by adjusting to their maximum rotational speed at the characteristic frequency of the rotating electrical field critical for the secreting cells in a given medium.

3. A process for determining cells secreting cellular contents such as proteins and/or glycoproteins, hormones, or growth factors, from a medium containing the secreting cells and other cells of the same species or genus, said process comprising:

providing at least three electrodes forming an intermediate space between them for a chamber containing the cells;

providing means connected to said electrodes to produce a rotating field of variable rotational frequency;

arranging said electrodes in such a way that the chamber space is exposed to a rotating electrical field produced by the electrodes;

exposing the cells to rotating electric field forces of variable rotational speeds;

differentiating a first group of cells secreting cellular contents from said other cells by means of the rotational behavior of said secreting cells which differs from that of said other cells.

4. The process of claim 1 wherein the intensity of the rotating field is variable.

5. The process of claim 1 wherein the voltages producing the rotating field are sinusoidal.

* * * * *